United States Patent
Bebot et al.

(10) Patent No.: US 9,833,400 B2
(45) Date of Patent: Dec. 5, 2017

(54) COSMETIC COMPOSITION COMPRISING A FIXING POLYMER AND A SPECIFIC THICKENER AND USES IN STYLING

(75) Inventors: Cécile Bebot, Clichy (FR); Mélanie Bellet, Paris (FR); Dorothée Pasquet, Bois Colombes (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 13/821,047

(22) PCT Filed: Sep. 6, 2011

(86) PCT No.: PCT/EP2011/065406
§ 371 (c)(1),
(2), (4) Date: May 28, 2013

(87) PCT Pub. No.: WO2012/032057
PCT Pub. Date: Mar. 15, 2012

(65) Prior Publication Data
US 2013/0243718 A1  Sep. 19, 2013

Related U.S. Application Data

(60) Provisional application No. 61/383,000, filed on Sep. 15, 2010.

(30) Foreign Application Priority Data

Sep. 6, 2010  (FR) ...................... 10 57062

(51) Int. Cl.
| A61K 8/72 | (2006.01) |
| A61Q 5/06 | (2006.01) |
| A61K 8/34 | (2006.01) |
| A61K 8/81 | (2006.01) |

(52) U.S. Cl.
CPC ............... *A61K 8/72* (2013.01); *A61K 8/34* (2013.01); *A61K 8/8147* (2013.01); *A61K 8/8152* (2013.01); *A61K 8/8182* (2013.01); *A61Q 5/06* (2013.01); *A61Q 5/065* (2013.01); *A61K 2800/594* (2013.01)

(58) Field of Classification Search
CPC . A61Q 5/06; A61Q 3/02; A61Q 19/00; A61Q 5/02; A61Q 5/04; A61Q 1/10; A61Q 11/00; A61Q 17/04; A61Q 19/002; A61Q 19/10; A61Q 5/00; A61Q 9/02; A61Q 17/00; A61Q 19/08; A61Q 5/12; A61Q 17/02
See application file for complete search history.

(56) References Cited

U.S. PATENT DOCUMENTS

| 2,047,398 A | 7/1936 | Voss et al. |
| 2,723,248 A | 11/1955 | Wright |
| 2,798,053 A | 7/1957 | Brown |
| 2,923,692 A | 2/1960 | Ackerman et al. |
| 3,579,629 A | 5/1971 | Pasero et al. |
| 3,589,578 A | 6/1971 | Kamphausen |
| 3,716,633 A | 2/1973 | Viout et al. |
| 3,810,977 A | 5/1974 | Levine et al. |
| 3,836,537 A | 9/1974 | Boerwinkle et al. |
| 3,910,862 A | 10/1975 | Barabas et al. |
| 3,915,921 A | 10/1975 | Schlatzer, Jr. |
| 3,925,542 A | 12/1975 | Viout et al. |
| 3,946,749 A | 3/1976 | Papantoniou |
| 3,966,403 A | 6/1976 | Papantoniou et al. |
| 3,966,404 A | 6/1976 | Papantoniou et al. |
| 3,990,459 A | 11/1976 | Papantoniou |
| 4,031,307 A | 6/1977 | DeMartino et al. |
| 4,128,631 A | 12/1978 | Lundmark et al. |
| 4,129,711 A | 12/1978 | Viout et al. |
| 4,131,576 A | 12/1978 | Iovine et al. |
| 4,137,208 A | 1/1979 | Elliott |
| 4,165,367 A | 8/1979 | Chakrabarti |
| 4,223,009 A | 9/1980 | Chakrabarti |
| 4,237,243 A | 12/1980 | Quack et al. |
| 4,282,203 A | 8/1981 | Jacquet et al. |
| 4,289,752 A | 9/1981 | Mahieu et al. |
| 4,509,949 A | 4/1985 | Huang et al. |
| 4,693,935 A | 9/1987 | Mazurek |
| 4,728,571 A | 3/1988 | Clemens et al. |
| 4,957,732 A | 9/1990 | Grollier et al. |
| 4,972,037 A | 11/1990 | Garbe et al. |
| 5,089,578 A | 2/1992 | Valint et al. |
| 5,538,717 A | 7/1996 | La Poterie |
| 6,106,813 A | 8/2000 | Mondet et al. |
| 6,166,093 A | 12/2000 | Mougin et al. |
| 6,319,959 B1 | 11/2001 | Mougin et al. |
| 6,372,876 B1 | 4/2002 | Kim et al. |
| 6,395,265 B1 | 5/2002 | Mougin et al. |
| 6,822,039 B1 | 11/2004 | Monfreux-Gaillard et al. |
| 7,063,834 B2 | 6/2006 | Mougin et al. |
| 2002/0150546 A1 | 10/2002 | Mougin et al. |
| 2003/0191271 A1 | 10/2003 | Mondet et al. |
| 2005/0142154 A1* | 6/2005 | Blatt et al. ............... 424/401 |
| 2010/0186764 A1* | 7/2010 | Pasquet ............ A61K 8/8147 132/203 |

FOREIGN PATENT DOCUMENTS

| DE | 2 330 956 | 1/1974 |
| DE | 196 25 810 | 1/1998 |
| EP | 0 080 976 | 6/1983 |
| EP | 0 186 507 | 7/1986 |
| EP | 0 342 834 | 11/1989 |

(Continued)

*Primary Examiner* — Audrea Buckley
(74) *Attorney, Agent, or Firm* — The Marbury Law Group, PLLC

(57) ABSTRACT

The present patent application relates to a hair styling composition, characterized in that it comprises: (i) one or more cationic fixing polymers, and (ii) one or more (meth) acrylic thickening polymers other than the fixing polymer or polymers (i), and (iii) from 5 to 27% by weight of water, with respect to the total weight of the cosmetic composition, (iv) from 70 to 90% by weight of one or more $C_1$ to $C_6$ alcohols, with respect to the total weight of the cosmetic composition.

14 Claims, No Drawings

(56) References Cited

FOREIGN PATENT DOCUMENTS

| | | | | |
|---|---|---|---|---|
| EP | 0 412 704 | 2/1991 | | |
| EP | 0 412 707 | 2/1991 | | |
| EP | 0 582 152 | 2/1994 | | |
| EP | 0 619 111 | 10/1994 | | |
| EP | 0 637 600 | 2/1995 | | |
| EP | 0 648 485 | 4/1995 | | |
| EP | 0 750 899 | 1/1997 | | |
| EP | 0 751 162 | 1/1997 | | |
| EP | 0 816 403 | 1/1998 | | |
| EP | 1 741 470 | 1/2007 | | |
| EP | 1741470 | * 1/2007 | .................... | 424/401 |
| FR | 1 222 944 | 6/1960 | | |
| FR | 1 400 366 | 4/1965 | | |
| FR | 1 564 110 | 3/1969 | | |
| FR | 1 580 545 | 9/1969 | | |
| FR | 2 077 143 | 10/1971 | | |
| FR | 2 198 719 | 4/1974 | | |
| FR | 2 265 781 | 10/1975 | | |
| FR | 2 265 782 | 10/1975 | | |
| FR | 2 350 384 | 12/1977 | | |
| FR | 2 357 241 | 2/1978 | | |
| FR | 2 393 573 | 1/1979 | | |
| FR | 2 416 723 | 9/1979 | | |
| FR | 2 439 798 | 5/1980 | | |
| FR | 2 743 297 | 7/1997 | | |
| FR | 2 939 660 | 6/2010 | | |
| GB | 839 805 | 6/1960 | | |
| GB | 922 457 | 4/1963 | | |
| GB | 1 021 400 | 3/1966 | | |
| GB | 1 408 388 | 10/1975 | | |
| GB | 1 572 626 | 7/1980 | | |
| JP | 2-295912 | 12/1990 | | |
| LU | 75370 | 2/1978 | | |
| LU | 75371 | 2/1978 | | |
| WO | 93/23009 | 11/1993 | | |
| WO | 93/23446 | 11/1993 | | |
| WO | 94/03510 | 2/1994 | | |
| WO | 95/00578 | 1/1995 | | |
| WO | 00/31154 | 6/2000 | | |

* cited by examiner

COSMETIC COMPOSITION COMPRISING A FIXING POLYMER AND A SPECIFIC THICKENER AND USES IN STYLING

This is a national stage application of PCT/EP2011/065406, filed internationally on Sep. 6, 2011, which claims priority to U.S. Provisional Application No. 61/383,000, filed on Sep. 15, 2010, as well as French Application FR 1057062, filed on Sep. 6, 2010.

The present invention relates to novel cosmetic compositions comprising one or more fixing polymers and one or more (meth)acrylic thickening polymers, and to the uses of these compositions, in particular in styling.

The present invention also relates to a method of styling keratin materials using these compositions.

The use of fixing polymers in styling and hair-fixing compositions is known. Nevertheless, the use of fixing polymers is not without disadvantage:
  the application of these polymers in the form of lacquers having a high alcohol content confers a dry feel on the hair after brushing; this undesirable phenomenon is particularly visible for dyed hair;
  the application of these polymers from conventional gel presents problems of tackiness associated with very long drying times;
  it is often difficult to ensure homogeneous distribution of these polymers over all the hair to be treated and obtain a uniform coating feel.

Unexpectedly and advantageously, the Applicant Company has demonstrated that the use of one or more fixing polymers with one or more (meth)acrylic thickening polymers in compositions having high levels of alcohols makes it possible to overcome the abovementioned disadvantages.

A subject-matter of the present invention is thus a cosmetic composition, characterized in that it comprises:
  (i) one or more cationic fixing polymers, and
  (ii) one or more (meth)acrylic thickening polymers other than the fixing polymer or polymers (i), and
  (iii) from 5 to 27% by weight of water, with respect to the total weight of the cosmetic composition,
  (iv) from 70 to 90% by weight of one or more $C_1$ to $C_6$ alcohols, with respect to the total weight of the cosmetic composition.

Another subject-matter of the present invention is a cosmetic composition, characterized in that it comprises:
  (i) one or more fixing polymers chosen among cationic, nonionic and amphoteric fixing polymers, and
  (ii) one or more (meth)acrylic thickening polymers other than the fixing polymer or polymers (i), and
  (iii) from 5 to 27% by weight of water, with respect to the total weight of the cosmetic composition,
  (iv) from 70 to 90% by weight of one or more $C_1$ to $C_6$ monoalcohols, with respect to the total weight of the cosmetic composition.

The compositions obtained are in the form of gels, mousses, sprays, creams or pastes.

Preferably, the compositions of the invention are not provided in the form of aerosol sprays.

More preferably still, the compositions of the invention are provided in the form of gels.

The compositions according to the present invention are easy to prepare and to apply. They remain satisfactorily localized, without runs, at the point of application. The compositions according to the present invention may be applied without a reduction in viscosity over time. They dry rapidly, without a tacky effect.

Moreover, the compositions according to the present invention make it possible to give the hairstyle a natural and long-lasting form retention.

Another subject-matter of the present invention is a method for styling keratin materials, preferably human keratin materials and in particular the hair, which uses the compositions according to the invention.

Another subject-matter of the present invention is the uses of the compositions according to the invention, especially for styling or shaping keratin materials, preferably human keratin materials and in particular the hair.

Other features, aspects, subject-matters and advantages of the invention will appear even more clearly on reading the description and examples that follow.

"(Meth)acrylic" is understood to mean, within the meaning of the present patent application, "acrylic or methacrylic".

Thickener

The composition according to the present invention also contains one or more (meth)acrylic thickening polymers.

(Meth)acrylic polymer or more simply acrylic polymer is understood to mean, within the meaning of the present invention, a polymer resulting from the polymerization of one or more monomers including one or more monomers of the structure (A):

(A)

$R_3$ denoting a hydrogen atom or a linear or branched $C_1$-$C_4$ alkyl radical, $R_4$ denoting a hydrogen atom, a linear or branched $C_1$-$C_4$ alkyl radical, an $NR_5R_6$ radical, or a linear or branched $C_1$-$C_{30}$ alkoxy radical, optionally substituted with one or more hydroxyl radicals or with a quaternary ammonium radical, $R_5$ and $R_6$ denote a hydrogen atom or an optionally oxyalkylenated $C_1$-$C_{30}$ alkyl radical, the alkyl radical possibly comprising a sulphonic group.

Preferably, $R_3$ denotes a hydrogen atom or a methyl radical.

For the purposes of the present invention, the expression "thickening polymer" means a polymer capable, by its presence, of increasing the viscosity of the medium by at least 50 centipoises at 25° C. and at a shear rate of 1 s$^{-1}$. Preferably, the thickening polymer has, at 1% in water or a 50/50 water/alcohol mixture by weight, a viscosity at 25° C. and at a shear rate of 1 s$^{-1}$ of greater than 100 centipoises. These viscosities may be measured in particular with viscometers or rheometers with cone-plate geometry.

The acrylic thickening polymers are chosen in particular from:
  (a) acrylic associative thickeners;
  (b) crosslinked acrylic acid homopolymers;
  (c) crosslinked copolymers of (meth)acrylic acid and of ($C_1$-$C_6$)alkyl acrylate;
  (d) nonionic homopolymers and copolymers comprising ethylenically unsaturated monomers of ester and/or amide type;
  (e) ammonium acrylate homopolymers or copolymers of ammonium acrylate and of acrylamide;
  (f) homopolymers and copolymers of (meth)acrylamido ($C_1$-$C_4$)alkylsulphonic acids;

(g) crosslinked methacryloyloxy($C_1$-$C_4$)alkyltri($C_1$-$C_4$) alkylammonium homopolymers and copolymers.

According to the invention, the expression "associative thickener" means an amphiphilic thickener comprising both hydrophilic units and hydrophobic units, in particular comprising at least one $C_8$-$C_{30}$ fatty chain and at least one hydrophilic unit.

Use may be made, as acrylic associative thickeners according to the invention, of the acrylic associative polymers chosen from (i) nonionic amphiphilic polymers comprising at least one fatty chain and at least one hydrophilic unit;

(ii) anionic amphiphilic polymers comprising at least one hydrophilic unit and at least one unit possessing a fatty chain;

(iii) cationic amphiphilic polymers comprising at least one hydrophilic unit and at least one unit possessing a fatty chain;

(iv) amphoteric amphiphilic polymers comprising at least one hydrophilic unit and at least one unit possessing a fatty chain;

the fatty chains containing from 10 to 30 carbon atoms.

(i) The acrylic nonionic amphiphilic polymers comprising at least one fatty chain and at least one hydrophilic unit are preferably chosen from:

(1) copolymers of $C_1$-$C_6$ alkyl methacrylates or acrylates and of amphiphilic monomers comprising at least one fatty chain (for example oxyethylenated ($C_8$-$C_{22}$)alkyl acrylates), for instance the oxyethylenated methyl methacrylate/stearyl acrylate copolymer sold by the company Goldschmidt under the name Antil 208;

(2) copolymers of hydrophilic methacrylates or acrylates and of hydrophobic monomers comprising at least one fatty chain (for example ($C_8$-$C_{22}$)alkyl (meth)acrylates), for instance polyethylene glycol methacrylate/lauryl methacrylate copolymer.

(ii) The acrylic anionic amphiphilic polymers can be chosen from those comprising at least one hydrophilic unit of unsaturated olefinic carboxylic acid type, and at least one hydrophobic unit of the type of ($C_{10}$-$C_{30}$)alkyl ester of an unsaturated carboxylic acid. They are preferably chosen from those for which the hydrophilic unit of unsaturated olefinic carboxylic acid type corresponds to the monomer of following formula (I)

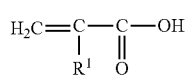

in which formula $R^1$ denotes H or $CH_3$ or $C_2H_5$, that is to say acrylic acid, methacrylic acid or ethacrylic acid units, and for which the hydrophobic unit of the type of ($C_{10}$-$C_{30}$)alkyl ester of an unsaturated carboxylic acid corresponds to the monomer of following formula (II):

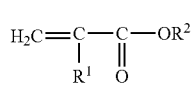

in which formula $R^1$ denotes H or $CH_3$ or $C_2H_5$ (i.e. acrylate, methacrylate or ethacrylate units) and preferably H (acrylate units) or $CH_3$ (methacrylate units), $R^2$ denoting a $C_{10}$-$C_{30}$ and preferably $C_{12}$-$C_{22}$ alkyl radical.

($C_{10}$-$C_{30}$)Alkyl esters of unsaturated carboxylic acids in accordance with the invention comprise, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic amphiphilic polymers of this type are disclosed and prepared, for example, according to U.S. Pat. No. 3,915,921 and U.S. Pat. No. 4,509,949.

The anionic amphiphilic polymers which can be used in the context of the present invention can more particularly denote polymers formed from a mixture of monomers comprising:

(i) acrylic acid and one or more esters of following formula (III):

in which $R^1$ denotes H or $CH_3$, $R^2$ denoting an alkyl radical containing from 12 to 22 carbon atoms, and a crosslinking agent, such as, for example, those constituted of from 95% to 60% by weight of acrylic acid (hydrophilic unit), 4% to 40% by weight of $C_{10}$-$C_{30}$ alkyl acrylate (hydrophobic unit), and 0% to 6% by weight of crosslinking polymerizable monomer, or 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer, (ii) essentially acrylic acid and lauryl methacrylate, such as the product formed from 66% by weight of acrylic acid and 34% by weight of lauryl methacrylate.

The said crosslinked agent is a monomer comprising a

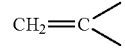

group with at least one other polymerizable group, the unsaturated bonds of which are not conjugated with respect to one another. Mention may be made in particular of polyallyl ethers such as, in particular, polyallyl sucrose and polyallyl pentaerythritol.

Among the said polymers above, the ones very particularly preferred according to the present invention are the products sold by the company Goodrich under the trade names Pemulen TR1, Pemulen TR2, Carbopol 1382, and more preferably still Pemulen TR1, and the product sold by the company S.E.P.C. under the name Coatex SX.

As fatty-chain anionic amphiphilic polymers, mention may also be made of the copolymer of methacrylic acid, methyl acrylate and dimethyl-meta-isopropenylbenzyl isocyanate of ethoxylated alcohol sold under the name Viscophobe DB 1000 by the company Amerchol.

Other fatty-chain anionic amphiphilic polymers that may be mentioned include those comprising at least one acrylic monomer containing sulphonic group(s), in free or partially or totally neutralized form and comprising at least one hydrophobic portion.

The hydrophobic portion present in the polymers of the invention preferably contains from 8 to 22 carbon atoms, more preferably still from 8 to 18 carbon atoms and more particularly from 12 to 18 carbon atoms.

Preferably, the sulphonic polymers in accordance with the invention are partially or totally neutralized with an inorganic base (sodium hydroxide, potassium hydroxide or aqueous ammonia) or an organic base such as mono-, di- or triethanolamine, an aminomethylpropanediol, N-methylglucamine, basic amino acids, for instance arginine and lysine, and mixtures of these compounds.

The sulphonic amphiphilic polymers in accordance with the invention generally have a number-average molecular weight ranging from 1000 to 20000000 g/mol, preferably ranging from 20000 to 5000000 g/mol and more preferably still from 100000 to 1500000 g/mol.

The sulphonic amphiphilic polymers according to the invention may or may not be crosslinked. Crosslinked amphiphilic polymers are preferably chosen.

When they are crosslinked, the crosslinking agents may be chosen from polyolefinically unsaturated compounds commonly used for the crosslinking of polymers obtained by free-radical polymerization. Mention may be made, for example, of divinylbenzene, diallyl ether, dipropylene glycol diallyl ether, polyglycol diallyl ethers, triethylene glycol divinyl ether, hydroquinone diallyl ether, ethylene glycol diacrylate di(meth)acrylate or tetraethylene glycol diacrylate di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allyl ethers of alcohols of the sugar series, or other allyl or vinyl ethers of polyfunctional alcohols, and also allyl esters of phosphoric and/or vinylphosphonic acid derivatives, or mixtures of these compounds.

Methylenebisacrylamide, allyl methacrylate or trimethylolpropane triacrylate (TMPTA) will be used more particularly. The degree of crosslinking will generally range from 0.01 mol % to 10 mol % and more particularly from 0.2 mol % to 2 mol % relative to the polymer.

The acrylic monomers containing sulphonic group(s) are chosen especially from (meth)acrylamido($C_1$-$C_{22}$)alkyl sulphonic acids and N—($C_1$-$C_{22}$)alkyl(meth)acrylamido($C_1$-$C_{22}$)alkylsulphonic acids, for instance undecylacrylamidomethanesulphonic acid, and also partially or totally neutralized forms thereof.

Use will more preferably be made of (meth)acrylamido ($C_1$-$C_{22}$)alkylsulphonic acids, such as, for example, acrylamidomethanesulphonic acid, acrylamidoethanesulphonic acid, acrylamidopropanesulphonic acid, 2-acrylamido-2-methylpropanesulphonic acid, methacrylamido-2-methylpropanesulphonic acid, 2-acrylamido-n-butanesulphonic acid, 2-acrylamido-2,4,4-trimethylpentanesulphonic acid, 2-methacrylamidododecylsulphonic acid, 2-acrylamido-2,6-dimethyl-3-heptanesulphonic acid, and also partially or totally neutralized forms thereof.

2-Acrylamido-2-methylpropanesulphonic acid (AMPS), and also partially or totally neutralized forms thereof, will more particularly be used.

The amphiphilic polymers in accordance with the invention may be chosen especially from random amphiphilic AMPS polymers modified by reaction with a $C_6$-$C_{22}$ n-monoalkylamine or di-n-alkylamine, and such as those described in Patent Application WO 00/31154; the polymers described in this application form part of the content of the present description. These polymers can also comprise other ethylenically unsaturated hydrophilic monomers chosen, for example, from (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

The polymers of the invention may be chosen from amphiphilic copolymers of AMPS and of at least one ethylenically unsaturated hydrophobic monomer comprising at least one hydrophobic portion containing from 8 to 50 carbon atoms, more preferably from 8 to 22 carbon atoms, more preferably still from 8 to 18 carbon atoms and more particularly 12 to 18 carbon atoms.

These same copolymers may also contain one or more ethylenically unsaturated monomers not comprising a fatty chain, such as (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

These copolymers are described in particular in Patent Application EP-A-750899, U.S. Pat. No. 5,089,578 and in the following publications by Yotaro Morishima:

"Self-assembling amphiphilic polyelectrolytes and their nanostructures—Chinese Journal of Polymer Science, Vol. 18, No. 40, (2000), 323-336."

"Micelle formation of random copolymers of sodium 2-(acrylamido)-2-methylpropanesulfonate and a nonionic surfactant macromonomer in water as studied by fluorescence and dynamic light scattering—Macromolecules, 2000, Vol. 33, No. 10, 3694-3704";

"Solution properties of micelle networks formed by nonionic moieties covalently bound to an polyelectrolyte: salt effects on rheological behavior—Langmuir, 2000, Vol. 16, No. 12, 5324-5332";

"Stimuli responsive amphiphilic copolymers of sodium 2-(acrylamido)-2-methylpropanesulfonate and associative macromonomers—Polym. Preprint, Div. Polym. Chem., 1999, 40(2), 220-221".

The ethylenically unsaturated hydrophobic monomers of these specific copolymers are preferably chosen from acrylates or acrylamides of following formula (IV):

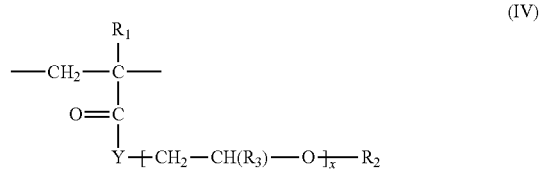

in which $R_1$ and $R_3$, which are identical or different, denote a hydrogen atom or a linear or branched $C_1$-$C_6$ alkyl radical (preferably methyl); Y denotes O or NH; $R_2$ denotes a hydrophobic hydrocarbon-based radical comprising at least from 8 to 50 carbon atoms, more preferably from 8 to 22 carbon atoms, more preferably still from 6 to 18 carbon atoms and more particularly from 12 to 18 carbon atoms; and x denotes a number of moles of alkylene oxide and varies from 0 to 100.

The $R_2$ radical is preferably chosen from linear $C_6$-$C_{18}$ alkyl radicals (for example n-hexyl, n-octyle, n-decyl, n-hexadecyl or n-dodecyl radicals); branched $C_6$-$C_{18}$ alkyl radicals; cyclic $C_6$-$C_{18}$ alkyl radicals (for example cyclododecane ($C_{12}$) or adamantane ($C_{10}$) radicals); $C_6$-$C_{18}$ alkylperfluorinated radicals (for example the group of formula —$(CH_2)_2$—$(CF_2)_9$—$CF_3$); the cholesteryl ($C_{27}$) radical or a cholesterol ester residue, such as the cholesteryl oxyhexanoate group; or polycyclic aromatic groups, such as naphthalene or pyrene. Among these radicals, the ones that are more particularly preferred are linear alkyl radicals and more particularly the n-dodecyl radical.

According to a particularly preferred form of the invention, the monomer of formula (IV) comprises at least one alkylene oxide unit (x≥1) and preferably a polyoxyalkylene chain. The polyoxyalkylene chain is preferably constituted of ethylene oxide units and/or of propylene oxide units and more particularly still constituted of ethylene oxide units. The number of oxyalkylene units generally ranges from 3 to 100, more preferably from 3 to 50 and more preferably still from 7 to 25.

Mention may be made, among these polymers, of:
copolymers, which may or may not be crosslinked and which may or may not be neutralized, comprising from 15 to 60% by weight of AMPS units and from 40 to 85% by weight of ($C_8$-$C_{16}$)alkyl(meth)acrylamide units or of ($C_8$-$C_{16}$)alkyl(meth)acrylate units, with respect to the polymer, such as those described in Application EP-A-750 899;
terpolymers comprising from 10 mol % to 90 mol % of acrylamide units, from 0.1 mol % to 10 mol % of AMPS units and from 5 mol % to 80 mol % of n-($C_6$-$C_{18}$)alkylacrylamide units, such as those described in U.S. Pat. No. 5,089,578.

Mention may also be made of copolymers of totally neutralized AMPS and of dodecyl methacrylate, and also crosslinked and non-crosslinked copolymers of AMPS and of n-dodecylmethacrylamide, such as those described in the Morishima papers mentioned above.

Mention will more particularly be made of the copolymers composed of 2-acrylamido-2-methylpropanesulphonic acid (AMPS) units of following formula (V):

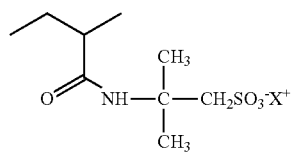

(V)

in which $X^+$ is a proton, an alkali metal cation, an alkaline earth metal cation or the ammonium ion,
and of units of following formula (VI):

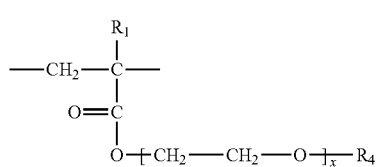

(VI)

in which x denotes an integer varying from 3 to 100, preferably from 5 to 8, and more preferably from 7 to 25; $R_1$ has the same meaning as that indicated above in formula (I) and $R_4$ denotes a linear or branched $C_6$-$C_{22}$ and more preferably $C_{10}$-$C_{22}$ alkyl.

The polymers which are particularly preferred are those for which x=25, $R_1$ denotes methyl and $R_4$ represents n-dodecyl; they are described in the abovementioned Morishima papers.

The polymers for which $X^+$ denotes sodium or ammonium are more particularly preferred.

(iii) The cationic amphiphilic polymers used in the present invention are preferably chosen from polyacrylates containing amine side groups.

The polyacrylates containing quaternized or non-quaternized amine side groups contain, for example, hydrophobic groups of the type of steareth-20 (polyoxyethylenated (20) stearyl alcohol) or ($C_{10}$-$C_{30}$)alkyl PEG-20 itaconate.

Examples of polyacrylates containing amine side chains that may be mentioned are the polymers 8781-124B or 9492-103 or Structure Plus from the company National Starch.

(iv) As amphoteric amphiphilic polymers containing at least one fatty chain, mention may be made of methacrylamidopropyltrimethylammonium chloride/acrylic acid/$C_{10}$-$C_{30}$ alkyl methacrylate copolymers, the alkyl radical preferably being a stearyl radical.

(b) Mention may be made, among crosslinked acrylic acid homopolymers, of those crosslinked by an allyl ether of an alcohol from the sugar series, such as, for example, the products sold under the names Carbopol 980, 981, 954, 2984 and 5984 by Goodrich or the products sold under the names Synthalen M and Synthalen K by 3 VSA.

(c) Mention may be made, among crosslinked copolymers of (meth)acrylic acid and of $C_1$-$C_6$ alkyl acrylate, of the product sold under the name Viscoatex 538C by Coatex, which is a crosslinked copolymer of methacrylic acid and of ethyl acrylate as a 38% aqueous dispersion of active material, or the product sold under the name Aculyn 33 by Rohm & Haas, which is a crosslinked copolymer of acrylic acid and of ethyl acrylate as a 28% aqueous dispersion of active material. Mention may be made more particularly of the crosslinked methacrylic acid/ethyl acrylate copolymer in the form of a 30% aqueous dispersion manufactured and sold under the name Carbopol Aqua SF-1 by the company Noveon.

(d) Mention may be made, among nonionic homopolymers or copolymers comprising ethylenically unsaturated monomers of ester and/or amide type, of the products sold under the names of: Cyanamer P250 by the company Cytec (polyacrylamide); PMMA MBX-8C by the company US Cosmetics (methyl methacrylate/ethylene glycol dimethacrylate copolymer); Acryloid B66 by the company Rohm & Haas (butyl methacrylate/methyl methacrylate copolymer); BPA 500 by the company Kobo (polymethyl methacrylate).

(e) Mention may be made, among ammonium acrylate homopolymers, of the product sold under the name Microsap PAS 5193 by Hoechst.

Among the copolymers of ammonium acrylate and of acrylamide that may be mentioned is the product sold under the name Bozepol C Nouveau or the product PAS 5193 sold by the company Hoechst (they are described and prepared in documents FR-2 416 723, U.S. Pat. No. 2,798,053 and U.S. Pat. No. 2,923,692).

(f) Poly(meth)acrylamido($C_1$-$C_4$)alkylsulphonic acids

According to the present invention, the poly(meth)acrylamido($C_1$-$C_4$)alkylsulphonic acid(s) is (are) preferably crosslinked.

Even more particularly, they are partially or totally neutralized.

These are water-soluble or water-swellable polymers. Mention may in particular be made, among these polymers, of:
polyacrylamidomethanesulphonic acid,
polyacrylamidoethanesulphonic acid,
polyacrylamidopropanesulphonic acid,
poly(2-acrylamido-2-methylpropanesulphonic acid),
poly(2-methacrylamido-2-methylpropanesulphonic acid),
poly(2-acrylamido-n-butanesulphonic acid).

Polymers of this type and especially crosslinked and partially or totally neutralized poly(2-acrylamido-2-methylpropanesulphonic acid)s are known, described and prepared in Patent Application DE-196 25 810.

They are generally characterized in that they comprise, distributed randomly:

a) from 90 to 99.9% by weight of units of following formula (VII):

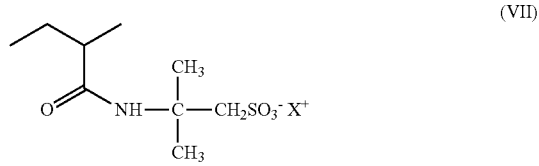

(VII)

in which $X^+$ denotes a cation or a mixture of cations, including $H^+$, b) from 0.01% to 10% by weight of at least one crosslinking unit containing at least two olefinic double bonds, the weight proportions being defined relative to the total weight of the polymer;

$X^+$ represents a cation or a mixture of cations chosen in particular from a proton, an alkali metal cation, a cation equivalent to that of an alkaline earth metal, or an ammonium ion.

The crosslinked and neutralized poly(2-acrylamido-2-methylpropanesulphonic acid) preferably comprises from 98% to 99.5% by weight of units of formula (I) and from 0.5% to 2% by weight of crosslinking units.

The crosslinking units containing at least two olefinic double bonds are chosen, for example, from dipropylene glycol diallyl ether, polyglycol diallyl ethers, triethylene glycol divinyl ether, hydroquinone diallyl ether, tetraallyloxyethane or other polyfunctional alcohol allyl or vinyl ethers, tetraethylene glycol diacrylate, triallylamine, trimethylolpropane diallyl ether, methylenebisacrylamide or divinylbenzene.

The crosslinking units having at least two olefinic double bonds are more particularly still chosen from those corresponding to the following general formula (VIII):

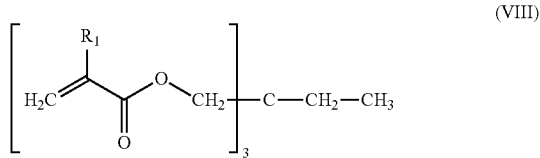

(VIII)

in which $R_1$ denotes a hydrogen atom or a $C_1$-$C_4$ alkyl and more particularly a methyl (trimethylolpropane triacrylate).

The crosslinked and partially or totally neutralized poly (2-acrylamido-2-methylpropanesulphonic acid)s are generally known under the names "Ammonium polyacrylamido-2-methylpropanesulphonate" or "Ammonium polyacryldimethyltauramide" (INCI name).

A product that is particularly preferred according to the invention is the one sold by the company Clariant under the trade name Hostacerin AMPS; this is a crosslinked poly(2-acrylamido-2-methylpropanesulphonic acid) partially neutralized with aqueous ammonia.

(g) Crosslinked polymers of methacryloyloxy($C_1$-$C_4$) alkyltri($C_1$-$C_4$)alkylammonium salts, such as the polymers obtained by homopolymerization of dimethylaminoethyl methacrylate quaternised by methyl chloride or by copolymerization of acrylamide with dimethylaminoethyl methacrylate quaternised by methyl chloride, the homo or the copolymerization being followed by a crosslinking by an olefinically unsaturated compound, in particular methylenebisacrylamide. Use may more particularly be made of a crosslinked acrylamide/methacryloyloxyethyltrimethylammonium chloride (20/80 by weight) copolymer in the form of a dispersion comprising 50% by weight of the said copolymer in mineral oil. This dispersion is sold under the name Salcare® SC 92 by the company Ciba. Use may also be made of a crosslinked homopolymer of methacryloyloxyethyltrimethylammonium chloride comprising approximately 50% by weight of the homopolymer in mineral oil or in a liquid ester. These dispersions are sold under the names Salcare® SC 95 and Salcare® SC 96 by CIBA.

Preferably, the (meth)acrylic thickening polymer(s) according to the invention is (are) anionic.

The (meth)acrylic thickening polymers are more particularly chosen from:
(a) acrylic associative thickeners;
(b) crosslinked acrylic acid homopolymers;
(c) crosslinked copolymers of (meth)acrylic acid and of ($C_1$-$C_6$)alkyl acrylate.

The composition according to the invention advantageously comprises from 0.05 to 20% by weight, preferably from 0.1 to 10% by weight and better still from 0.3 to 5% by weight of one or more (meth)acrylic thickening polymers, with respect to the total weight of the composition.

Fixing Polymer

As indicated above, the compositions comprise fixing polymers other than the thickening polymers used according to the invention. The expression "fixing polymer" is understood within the meaning of the present invention to mean any polymer that makes it possible to give a shape to the hair or to retain the hair in a given shape.

All the anionic, cationic, amphoteric and nonionic fixing polymers and mixtures thereof used in the art may be used in the compositions according to the present patent application.

The fixing polymers may be soluble in the cosmetically acceptable medium or insoluble in this same medium and used in this case in the form of dispersions of solid or liquid particles of polymer (latex or pseudolatex).

The anionic fixing polymers generally used are polymers containing groups derived from carboxylic, sulphonic or phosphoric acid, and have a number-average molecular weight of between approximately 500 and 5000000.

The anionic fixing polymers containing carboxylic groups that are preferred according to the invention are:

A) copolymers of acrylic acid and of acrylamide sold in the form of sodium salts thereof under the names Reten 421, 423 or 425 by Hercules, or sodium salts of polyhydroxycarboxylic acids;

B) copolymers of acrylic or methacrylic acid with a monoethylenic monomer such as ethylene, styrene, vinyl esters, acrylic or methacrylic acid esters, optionally grafted onto a polyalkylene glycol such as polyethylene glycol and optionally crosslinked. Such polymers are described in particular in French Patent 1 222 944 and German Patent Application 2 330 956, the copolymers of this type comprising an optionally N-alkylated and/or N-hydroxyalkylated acrylamide unit in their chain as described in particular in Luxembourg Patent Applications 75370 and 75371 or provided under the name Quadramer by the company American Cyanamid. Mention may also be made of the acrylic acid/ethyl acrylate/N-tert-butylacrylamide terpolymers such as Ultrahold Strong sold by the company BASF.

Mention may also be made of copolymers of acrylic acid and of $C_1$-$C_4$ alkyl methacrylate and terpolymers of vinylpyrrolidone, of acrylic acid and of $C_1$-$C_{20}$ alkyl methacrylate, for example lauryl methacrylate, such as the product sold by the company ISP under the name Acrylidone® LM, and methacrylic acid/ethyl acrylate/tert-butyl acrylate terpolymers such as the product sold under the name Luvimer® 100 P by the company BASF;

Mention may also be made of methacrylic acid/acrylic acid/ethyl acrylate/methyl methacrylate copolymers as an aqueous dispersion, sold under the name Amerhold® DR 25 by the company Amerchol.

C) crotonic acid copolymers, such as those comprising vinyl acetate or propionate units in their chain and optionally other monomers such as allyl esters or methallyl esters, vinyl ether or vinyl ester of a linear or branched saturated carboxylic acid with a long hydrocarbon chain such as those containing at least 5 carbon atoms, it being possible for these polymers optionally to be grafted or crosslinked, or alternatively another monomer which is a vinyl, allyl or methallyl ester of an α- or β-cyclic carboxylic acid. Such polymers are described, inter alia, in French Patents 1 222 944, 1 580 545, 2 265 782, 2 265 781, 1 564 110 and 2 439 798. Commercial products that come under this category are the resins 28-29-30, 26-13-14 and 28-13-10 sold by the company National Starch;

D) copolymers of $C_4$-$C_8$ monounsaturated carboxylic acids or anhydrides chosen from:

copolymers comprising (i) one or more maleic, fumaric or itaconic acids or anhydrides and (ii) at least one monomer selected from vinyl esters, vinyl ethers, vinyl halides, phenylvinyl derivatives, acrylic acid and its esters, the anhydride functional groups of these copolymers optionally being monoesterified or monoamidated. Such polymers are described, in particular, in U.S. Pat. Nos. 2,047,398, 2,723,248 and 2,102,113, and GB Patent 839 805. Commercial products are especially those sold under the names Gantrez® AN or ES by the company ISP;

copolymers comprising (i) one or more maleic, citraconic or itaconic anhydride units and (ii) one or more monomers chosen from allyl or methallyl esters optionally comprising one or more acrylamide, methacrylamide, α-olefin, acrylic or methacrylic ester, acrylic or methacrylic acid or vinylpyrrolidone groups in their chain, the anhydride functional groups of these copolymers optionally being monoesterified or monoamidated.

These polymers are described, for example, in French Patents 2 350 384 and 2 357 241 of the Applicant;

E) polyacrylamides comprising carboxylate groups.

F) Homopolymers and copolymers comprising sulphonic groups, such as polymers comprising vinyl sulphonic, styrenesulphonic, naphthalenesulphonic or acrylamidoalkylsulphonic units. These polymers can be chosen in particular from:

polyvinylsulphonic acid salts having a molecular weight of between approximately 1000 and 100000, and also the copolymers with an unsaturated comonomer such as acrylic or methacrylic acids and their esters, and also acrylamide or its derivatives, vinyl ethers and vinylpyrrolidone;

polystyrenesulphonic acid salts such as the sodium salts that are sold for example under the names Flexan® 500 and Flexan® 130 by National Starch. These compounds are described in Patent FR 2 198 719;

polyacrylamidesulphonic acid salts, such as those mentioned in U.S. Pat. No. 4,128,631 and more particularly polyacrylamidoethylpropanesulphonic acid sold under the name Cosmedia Polymer HSP 1180 by Henkel.

As another anionic fixing polymer that can be used according to the invention, mention may be made of the branched block anionic polymer sold under the name Fixate G-100 by the company Lubrizol.

According to the invention, the anionic fixing polymers are preferably chosen from copolymers of acrylic acid or of acrylic esters, such as the acrylic acid/ethyl acrylate/N-tert-butylacrylamide terpolymers sold especially under the name Ultrahold® Strong by the company BASF, copolymers derived from crotonic acid, such as the vinyl acetate/vinyl tert-butylbenzoate/crotonic acid terpolymers and the crotonic acid/vinyl acetate/vinyl neododecanoate terpolymers sold especially under the name Resin 28-29-30 by the company National Starch, polymers derived from maleic, fumaric or itaconic acids or anhydrides with vinyl esters, vinyl ethers, vinyl halides, phenylvinyl derivatives and acrylic acid and esters thereof, such as the methyl vinyl ether/monoesterified maleic anhydride copolymers sold, for example, under the name Gantrez® by the company ISP, the copolymers of methacrylic acid and of methyl methacrylate sold under the name Eudragit® L by the company Rohm Pharma, the copolymers of methacrylic acid and of ethyl acrylate sold under the name Luvimer® MAEX or MAE by the company BASF, the vinyl acetate/crotonic acid copolymers sold under the name Luviset CA 66 by the company BASF, the vinyl acetate/crotonic acid copolymers grafted with polyethylene glycol sold under the name Aristoflex® A by the company BASF, and the polymer sold under the name Fixate G-100 L by the company Lubrizol.

The cationic fixing film-forming polymers that can be used according to the present invention are preferably chosen from polymers comprising primary, secondary, tertiary and/or quaternary amine groups forming part of the polymer chain or directly attached thereto, and having a molecular weight of between 500 and about 5000000 and preferably between 1000 and 3000000.

Among these polymers, mention may be made more particularly of the following cationic polymers:

(1) homopolymers or copolymers derived from acrylic or methacrylic esters or amides and comprising at least one of the units of the following formulae:

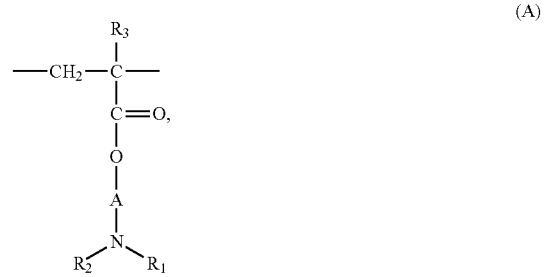

(A)

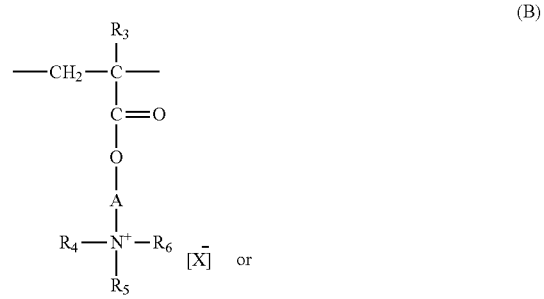

(B)

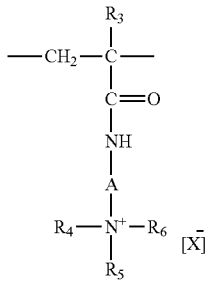

(C)

in which:

R₃ denotes a hydrogen atom or a CH₃ radical;

A is a linear or branched alkyl group comprising from 1 to 6 carbon atoms or a hydroxyalkyl group comprising from 1 to 4 carbon atoms;

R₄, R₅ and R₆, which may be identical or different, represent an alkyl group having from 1 to 18 carbon atoms or a benzyl radical;

R₁ and R₂, which may be identical or different, each represent a hydrogen atom or an alkyl group having from 1 to 6 carbon atoms;

X denotes a methosulphate anion or a halide such as chloride or bromide.

The copolymers of the family (1) also contain one or more units deriving from comonomers that may be chosen from the family of acrylamides, methacrylamides, diacetone acrylamides, acrylamides and methacrylamides substituted on the nitrogen with lower (C₁-C₄) alkyl groups, groups derived from acrylic or methacrylic acids or esters thereof, vinyllactams such as vinylpyrrolidone or vinylcaprolactam, and vinyl esters.

Thus, among these copolymers of the family (1), mention may be made of:

copolymers of acrylamide and of dimethylaminoethyl methacrylate quaternized with dimethyl sulphate or with a methyl halide, such as the product sold under the name Hercofloc® by the company Hercules, copolymers of acrylamide and of methacryloyloxyethyltrimethylammonium chloride, described, for example, in Patent Application EP-A-080 976 and sold under the name Bina Quat P 100 by the company Ciba Geigy, the copolymer of acrylamide and of methacryloyloxyethyltrimethylammonium methosulphate, such as the product sold under the name Reten by the company Hercules, quaternized or non-quaternized vinylpyrrolidone/dialkylaminoalkyl acrylate or methacrylate copolymers, such as the products sold under the name Gafquat® by the company ISP, such as, for example, Gafquat® 734 or Gafquat® 755, or alternatively the products known as Copolymer® 845, 958 and 937. These polymers are described in detail in French Patents 2 077 143 and 2 393 573, fatty-chain polymers containing a vinylpyrrolidone unit, such as the products sold under the name Styleze W20 and Styleze W10 by the company ISP, dimethylaminoethyl methacrylate/vinylcaprolactam/vinylpyrrolidone terpolymers, such as the product sold under the name Gaffix VC 713 by the company ISP, and quaternized vinylpyrrolidone/dimethylaminopropylmethacrylamide copolymers, such as the products sold under the name Gafquat® HS 100 by the company ISP;

(2) non-cellulosic cationic polysaccharides, preferably containing quaternary ammonium, such as those described in U.S. Pat. Nos. 3,589,578 and 4,031,307, such as guar gums containing trialkylammonium cationic groups. Such products are sold in particular under the trade names Jaguar C13 S, Jaguar C 15 and Jaguar C 17 by the company Meyhall.

(3) quaternary copolymers of vinylpyrrolidone and of vinylimidazole.

(4) chitosans or salts thereof; the salts that can be used are, in particular, chitosan acetate, lactate, glutamate, gluconate or pyrrolidonecarboxylate.

Among these compounds, mention may be made of chitosan having a degree of deacetylation of 90.5% by weight, sold under the name Kytan Brut Standard by the company Aber Technologies, and chitosan pyrrolidonecarboxylate sold under the name Kytamer® PC by the company Amerchol.

(5) cationic cellulose derivatives such as copolymers of cellulose or of cellulose derivatives grafted with a water-soluble monomer comprising a quaternary ammonium, and disclosed in particular in U.S. Pat. No. 4,131,576, such as hydroxyalkylcelluloses, for instance hydroxymethyl-, hydroxyethyl- or hydroxypropylcelluloses, grafted in particular with a methacryloyloxyethyltrimethylammonium, methacrylamidopropyltrimethylammonium or dimethyldiallylammonium salt.

The products sold corresponding to this definition are, more particularly, the products sold under the name Celquat L 200 and Celquat H 100 by the company National Starch.

The amphoteric fixing polymers that can be used in accordance with the invention can be selected from polymers comprising units B and C distributed randomly in the polymer chain, where B denotes a unit deriving from a monomer comprising at least one basic nitrogen atom and C denotes a unit deriving from an acid monomer comprising one or more carboxylic or sulphonic groups, or alternatively B and C can denote groups deriving from carboxybetaine or sulphobetaine zwitterionic monomers;

B and C can also denote a cationic polymer chain comprising primary, secondary, tertiary or quaternary amine groups, in which at least one of the amine groups bears a carboxylic or sulphonic group connected via a hydrocarbon group, or alternatively B and C form part of a chain of a polymer containing an α,β-dicarboxylic ethylene unit in which one of the carboxylic groups has been made to react with a polyamine comprising one or more primary or secondary amine groups.

The amphoteric fixing polymers corresponding to the definition given above that are more particularly preferred are selected from the following polymers:

(1) copolymers having acidic vinyl units and basic vinyl units, such as those resulting from the copolymerization of a monomer derived from a vinyl compound bearing a carboxylic group, such as, more particularly, acrylic acid, methacrylic acid, maleic acid, α-chloroacrylic acid, and of a basic monomer derived from a substituted vinyl compound containing at least one basic atom, such as, more particularly, dialkylaminoalkyl methacrylate and acrylate, dialkylaminoalkylmethacrylamides and -acrylamides. Such compounds are described in U.S. Pat. No. 3,836,537.

(2) polymers comprising units deriving from:

a) at least one monomer selected from acrylamides or methacrylamides substituted on the nitrogen atom by an alkyl group, b) at least one acidic comonomer containing one or more reactive carboxylic groups, and c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides that are more particularly preferred according to the invention are compounds in which the alkyl groups contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, the alkyl having 1 to 4 carbon atoms, of maleic or fumaric acids or anhydrides.

The preferred basic comonomers are aminoethyl, butylaminoethyl, N,N-dimethylaminoethyl and N-tert-butylaminoethylmethacrylates.

Use is made particularly of the copolymers whose CTFA (4th edition, 1991) name is octylacrylamide/acrylates/butylaminoethyl methacrylate copolymer, such as the products sold under the name Amphomer® or Lovocryl® 47 by the company National Starch.

(3) crosslinked and acylated polyaminoamides, partially or totally, deriving from polyaminoamides of general formula:

$$+CO—R_{10}—CO—Z+ \quad (IX)$$

in which $R_{10}$ represents a divalent group derived from a saturated dicarboxylic acid, an aliphatic mono- or dicarboxylic acid containing an ethylenic double bond, an ester of a lower alkanol, having 1 to 6 carbon atoms, of these acids, or a group deriving from the addition of any one of the said acids to a bis(primary) or bis(secondary) amine, and Z denotes a group deriving from a bis(primary), mono- or bis(secondary) polyalkylenepolyamine and preferably represents:

a) in proportions of from 60 to 100 mol %, the group:

where x=2 and p=2 or 3, or alternatively x=3 and p=2 this group deriving from diethylenetriamine, from triethylenetetraamine or from dipropylenetriamine;

b) in proportions of from 0 to 40 mol %, the group (X) above in which x=2 and p=1 and which is derived from ethylenediamine, or the group deriving from piperazine:

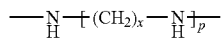

c) in proportions of from 0 to 20 mol %, the —NH—$(CH_2)_6$—NH— group deriving from hexamethylenediamine, these polyaminoamides being crosslinked by addition reaction of a difunctional crosslinking agent chosen from epihalohydrins, diepoxides, dianhydrides and bis-unsaturated derivatives, using from 0.025 to 0.35 mol of crosslinking agent per amine group of the polyaminoamide, and acylated by the action of acrylic acid, chloroacetic acid or an alkanesultone, or salts thereof.

The saturated carboxylic acids are preferably selected from acids having 6 to 10 carbon atoms, such as adipic acid, 2,2,4-trimethyladipic acid and 2,4,4-trimethyladipic acid, terephthalic acid, acids containing an ethylenic double bond such as, for example, acrylic acid, methacrylic acid or itaconic acid.

The alkanesultones used in the acylation are preferably propanesultone or butanesultone; the salts of the acylating agents are preferably the sodium or potassium salts.

(4) polymers comprising zwitterionic units of formula:

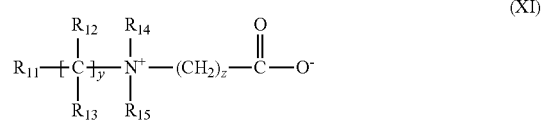

in which $R_{11}$ denotes a polymerizable unsaturated group such as an acrylate, methacrylate, acrylamide or methacrylamide group, y and z represent an integer from 1 to 3, $R_{12}$ and $R_{13}$ represent a hydrogen atom, a methyl, ethyl or propyl group, $R_{14}$ and $R_{15}$ represent a hydrogen atom or an alkyl group so that the sum of the carbon atoms in $R_{14}$ and $R_{15}$ does not exceed 10.

The polymers comprising such units can also comprise units derived from non-zwitterionic monomers such as dimethyl- or diethylaminoethyl acrylate or methacrylate or alkyl acrylates or methacrylates, acrylamides or methacrylamides, or vinyl acetate.

By way of example, mention may be made of the methyl methacrylate/methyl dimethylcarboxymethylammonioethyl methacrylate copolymers such as the product sold under the name Diaformer Z301 by the company Sandoz.

(5) polymers derived from chitosan comprising monomer units corresponding to the following formulae:

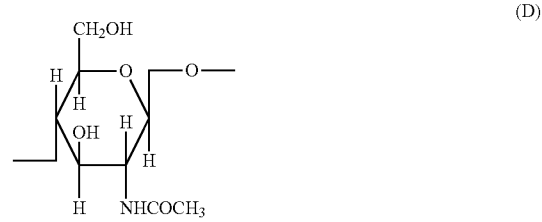

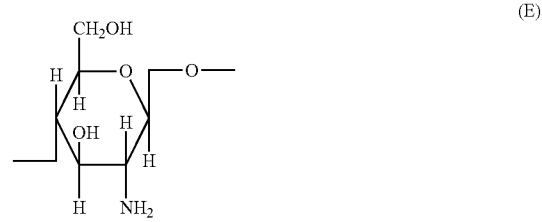

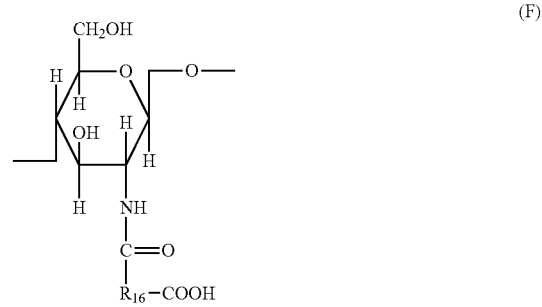

the unit (D) being present in proportions of between 0 and 30%, the unit (E) in proportions of between 5% and 50% and the unit (F) in proportions of between 30% and 90%, it being understood that, in this unit (F), $R_{16}$ represents a group of formula:

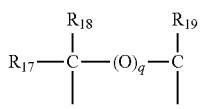

in which, if q=0, $R_{17}$, $R_{18}$ and $R_{19}$, which are identical or different, each represent a hydrogen atom, a methyl, hydroxyl, acetoxy or amino residue, a monoalkylamine residue or a dialkylamine residue that are optionally interrupted by one or more nitrogen atoms and/or optionally substituted by one or more amine, hydroxyl, carboxyl, alkylthio or sulphonic groups, an alkylthio residue in which the alkyl group bears an amino residue, at least one of the groups $R_{17}$, $R_{18}$ and $R_{19}$ being, in this case, a hydrogen atom;

or, if q=1, $R_{17}$, $R_{18}$ and $R_{19}$ each represent a hydrogen atom, as well as the salts formed by these compounds with bases or acids.

(6) polymers with units corresponding to the general formula (XII) are described, for example, in French Patent 1 400 366:

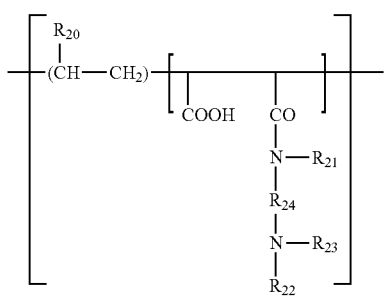

in which $R_{20}$ represents a hydrogen atom, a $CH_3O$, $CH_3CH_2O$ or phenyl group, $R_{21}$ denotes a hydrogen atom or a lower alkyl group such as methyl or ethyl, $R_{22}$ denotes a hydrogen atom or a lower $C_1$-$C_6$ alkyl group such as methyl or ethyl, $R_{23}$ denotes a lower $C_1$-$C_6$ alkyl group such as methyl or ethyl or a group corresponding to the formula: —$R_{24}$—$N(R_{22})_2$, $R_{24}$ representing a —$CH_2$—$CH_2$—, —$CH_2$—$CH_2$—$CH_2$— or —$CH_2$—$CH(CH_3)$— group, and $R_{22}$ having the abovementioned meanings.

(7) polymers derived from the N-carboxyalkylation of chitosan, such as N-carboxymethylchitosan or N-carboxybutylchitosan, sold under the name "Evalsan" by the company Jan Dekker.

(8) amphoteric polymers of the type -D-X-D-X— chosen from:

a) polymers obtained by the action of chloroacetic acid or sodium chloroacetate on compounds comprising at least one unit of formula:

-D-X-D-X-D- (XIII)

where D denotes a group

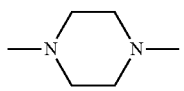

and X denotes the symbol E or E', E or E', which may be identical or different, denoting a divalent group that is an alkylene group with a straight or branched chain containing up to 7 carbon atoms in the main chain, which is unsubstituted or substituted by hydroxyl groups and which can additionally comprise oxygen, nitrogen and sulphur atoms and from 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups.

b) polymers of formula:

-D-X-D-X— (XIV)

where D denotes a group

and X denotes the symbol E or E' and at least once E'; E having the meaning given above and E' being a divalent group that is an alkylene group with a straight or branched chain having up to 7 carbon atoms in the main chain, which is unsubstituted or substituted with one or more hydroxyl groups and containing one or more nitrogen atoms, the nitrogen atom being substituted with an alkyl chain that is optionally interrupted by an oxygen atom and necessarily comprising one or more carboxyl functional groups or one or more hydroxyl functional groups and betainized by reaction with chloroacetic acid or sodium chloroacetate.

(9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkylaminoalkanol. These copolymers can also comprise other vinyl comonomers such as vinylcaprolactam.

Among the amphoteric fixing polymers mentioned above that are most particularly preferred according to the invention, mention will be made of those of family (3), such as the copolymers whose CTFA name is octylacrylamide/acrylates/butylaminoethyl methacrylate copolymer, such as the products sold under the names Amphomer®, Amphomer® LV 71 or Lovocryl® 47 by the company National Starch, and those of family (4), such as the methyl methacrylate/methyl dimethylcarboxymethylammonioethyl methacrylate copolymers, sold, for example, under the name Diaformer Z301 by the company Sandoz.

The nonionic fixing polymers that may be used according to the present invention are selected, for example, from:
  polyalkyloxazolines;
  vinyl acetate homopolymers;
  vinyl acetate copolymers, such as, for example, copolymers of vinyl acetate and of acrylic ester, copolymers of vinyl acetate and of ethylene, or copolymers of vinyl acetate and of maleic ester, for example of dibutyl maleate;
  homopolymers and copolymers of acrylic esters, such as, for example, copolymers of alkyl acrylates and of alkyl methacrylates, such as the products provided by the company Rohm & Haas under the names Primal® AC-261 K and Eudragit® NE 30 D, by the company BASF under the name 8845, or by the company Hoechst under the name Appretan® N9212;
  copolymers of acrylonitrile and of a nonionic monomer selected, for example, from butadiene and alkyl (meth)

acrylates; mention may be made of the products provided under the name CJ 0601 B by the company Rohm & Haas;

styrene homopolymers;

styrene copolymers, such as, for example, copolymers of styrene and of alkyl (meth)acrylate, such as the products Mowilith® LDM 6911, Mowilith® DM 611 and Mowilith® LDM 6070 provided by the company Hoechst, and the products Rhodopas® SD 215 and Rhodopas® DS 910 provided by the company Rhône-Poulenc; copolymers of styrene, of alkyl methacrylate and of alkyl acrylate; copolymers of styrene and of butadiene; or copolymers of styrene, of butadiene and of vinylpyridine;

polyamides;

vinyllactam homopolymers such as vinylpyrrolidone homopolymers and such as the polyvinylcaprolactam sold under the name Luviskol® Plus by the company BASF; and vinyllactam copolymers such as a poly(vinylpyrrolidone/vinyllactam) copolymer sold under the trade name Luvitec® VPC 55K65W by the company BASF, poly(vinylpyrrolidone/vinyl acetate) copolymers, such as those sold under the name PVPVA® S630L by the company ISP, Luviskol® VA 73, VA 64, VA 55, VA 37 and VA 28 by the company BASF; and poly(vinylpyrrolidone/vinyl acetate/vinyl propionate) terpolymers, such as, for example, the product sold under the name Luviskol® VAP 343 by the company BASF.

The alkyl groups of the nonionic polymers mentioned above preferably have from 1 to 6 carbon atoms.

According to the invention, it is also possible to use fixing polymers of grafted silicone type comprising a polysiloxane portion and a portion consisting of a non-silicone organic chain, one of the two portions constituting the main chain of the polymer and the other being grafted onto the said main chain.

These polymers are described, for example, in patent applications EP-A-0 412 704, EP-A-0 412 707, EP-A-0 640 105 and WO 95/00578, EP-A-0 582 152 and WO 93/23009 and U.S. Pat. No. 4,693,935, U.S. Pat. No. 4,728,571 and U.S. Pat. No. 4,972,037.

These polymers may be amphoteric, anionic or nonionic, and are preferably anionic or nonionic.

Such polymers are, for example, copolymers that can be obtained by free radical polymerization from the monomer mixture formed from:

a) 50 to 90% by weight of tert-butyl acrylate;
b) 0 to 40% by weight of acrylic acid;
c) 5 to 40% by weight of a silicone macromer of formula:

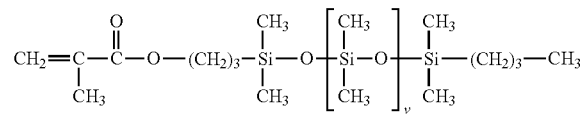

in which v is a number ranging from 5 to 700, the weight percentages being calculated relative to the total weight of the monomers.

Other examples of grafted silicone polymers are, in particular, polydimethylsiloxanes (PDMSs) onto which are grafted, via a thiopropylene-type connecting link, mixed polymer units of the poly(meth)acrylic acid type and of the polyalkyl (meth)acrylate type and polydimethylsiloxanes (PDMSs) onto which are grafted, via a thiopropylene-type connecting link, polymer units of the polyisobutyl (meth)acrylate type.

Another type of silicone fixing polymer that may be mentioned is the product Luviflex® Silk sold by the company BASF.

As fixing polymers it is also possible to use functionalized or non-functionalized, cationic, nonionic, anionic or amphoteric, silicone or non-silicone polyurethanes, or mixtures thereof.

The polyurethanes particularly intended by the present invention are those disclosed in patent applications EP 0 751 162, EP 0 637 600, EP 0 648 485 and FR 2 743 297, of which the Applicant is the Proprietor, and in patent applications EP 0 656 021 and WO 94/03510 from the company BASF and EP 0 619 111 from the company National Starch.

As polyurethanes that are particularly well suited to the present invention, mention may be made of the products sold under the names Luviset Pur® and Luviset® Si Pur by the company BASF.

In a first alternative form of the invention, the fixing polymer or polymers of the invention are nonionic or amphoteric or cationic and preferably cationic.

In a second alternative form of the invention, the fixing polymer or polymers of the invention do not result from monomers of formula (A).

The concentration of fixing polymer(s) used in the compositions according to the present invention is between 0.1% and 20% and preferably between 0.5% and 10% by weight relative to the total weight of the composition.

Water and Alcohol

The cosmetic composition of the invention comprises water in amounts ranging from 5 to 27% by weight, with respect to the total weight of the composition.

Preferably, the water content varies from 5 to 15% by weight, with respect to the total weight of the composition.

The cosmetic composition according to the invention additionally comprises one or more $C_2$ to $C_6$ alcohols in an amount ranging from 70 to 90% by weight, with respect to the total weight of the composition.

Preferably, the content of $C_2$ to $C_6$ alcohols varies from 75 to 85% by weight, with respect to the total weight of the composition.

The $C_2$ to $C_6$ alcohol is preferably a monoalcohol. It is preferably chosen from ethanol or isopropanol. More preferably still, the $C_2$-$C_6$ alcohol is ethanol.

Additives

The compositions according to the invention can also comprise other cosmetically acceptable adjuvants, such as, for example, ionic or nonionic surfactants, additional thickening agents other than the (meth)acrylic thickening polymers used in the compositions according to the present patent application, ethoxylated or nonethoxylated fatty alcohols, cothickening agents, penetrating agents, fragrances, colourants, plasticizers, buffers and various conventional adjuvants, such as waxes, volatile or non-volatile and linear, branched or cyclic silicones which are organomodified, in particular alkoxylated, modified by amine groups or unmodified, for example silicone gums, ceramides, pseudo-ceramides, vegetable, mineral or synthetic oils, vitamins or provitamines, such as panthenol, opacifying agents, reducing agents, emulsifiers, preservatives, inorganic fillers, pearlescent agents, glitter, sunscreens, proteins, moisturizing agents, emollients, softening agents, antifoaming agents, antiperspirants, agents for combating free radicals, bactericides, sequestering agents, anti-dandruff agents, antioxidants, basifying agents, acidifying agents and any other additive conventionally used in cosmetic compositions intended to be applied to the hair.

The surfactants that can be used in the composition according to the present invention may be anionic, nonionic, amphoteric or cationic surfactants, or mixtures thereof.

The term "anionic surfactant" means a surfactant comprising, as ionic or ionizable groups, only anionic groups. These anionic groups are preferably chosen from the following groups: $CO_2H$, $CO_2^-$, $SO_3H$, $SO_3^-$, $OSO_3H$, $OSO_3^-$, $H_2PO_3$, $HPO_3^-$, $PO_3^{2-}$, $H_2PO_2$, $HPO_2$, $HPO_2^-$, $PO_2^-$, $POH$, $PO^-$.

As examples of anionic surfactants that may be used in the composition according to the invention, mention may be made of alkyl sulphates, alkyl ether sulphates, alkylamido ether sulphates, alkylaryl polyether sulphates, monoglyceride sulphates, alkylsulphonates, alkylamidesulphonates, alkylarylsulphonates, α-olefinsulphonates, paraffinsulphonates, alkyl sulphosuccinates, alkyl ether sulphosuccinates, alkylamide sulphosuccinates, alkyl sulphoacetates, acyl sarcosinates, acyl glutamates, alkyl sulphosuccinamates, acyl isethionates and N-acyltaurates, salts of alkyl monoesters of polyglycoside-polycarboxylic acids, acyl lactylates, D-galactoside-uronic acid salts, alkyl ether carboxylic acid salts, alkylaryl ether carboxylic acid salts, alkylamido ether carboxylic acid salts; and the corresponding non-salified forms of all these compounds; the alkyl and acyl groups of all these compounds comprising from 6 to 24 carbon atoms and the aryl group denoting a phenyl group.

These compounds may be oxyethylenated and then preferably comprise from 1 to 50 ethylene oxide units.

The salts of $C_{6-24}$ alkyl monoesters of polyglycoside-polycarboxylic acids may be chosen from $C_{6-24}$ alkyl polyglycoside citrates, $C_{6-24}$ alkyl polyglycoside tartrates and $C_{6-24}$ alkyl polyglycoside sulphosuccinates.

When the anionic surfactant(s) (ii) are in salt form, it/they may be chosen from the alkali metal salts such as the sodium or potassium salt and preferably the sodium salt, the ammonium salts, the amine salts and in particular amino alcohol salts or the alkaline earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline earth metal salts and in particular the sodium or magnesium salts are preferably used.

Among the anionic surfactants, it is preferred, according to the invention, to use alkyl sulphate salts and alkyl ether sulphate salts and mixtures thereof.

The nonionic surfactants which can be used in the context of the present invention are themselves also compounds well known per se (see in particular in this regard "Handbook of Surfactants" by M. R. Porter, published by Blackie & Son (Glasgow and London), 1991, pp. 116-178). They can in particular be chosen from polyethoxylated, polypropoxylated or polyglycerolated fatty alcohols, α-diols, ($C_1$-$C_{20}$) alkylphenols or acids having a fatty chain comprising, for example, from 8 to 18 carbon atoms, it being possible for the number of ethylene oxide or propylene oxide groups to range, in particular, from 2 to 50 and it being possible for the number of glycerol groups to range, in particular, from 2 to 30. Mention may also be made of copolymers of ethylene oxide and of propylene oxide or condensates of ethylene oxide and of propylene oxide with fatty alcohols; polyethoxylated fatty amides preferably having from 2 to 30 mol of ethylene oxide; polyglycerolated fatty amides comprising, on average, from 1 to 5 glycerol groups and in particular from 1.5 to 4; polyethoxylated fatty amines preferably having from 2 to 30 mol of ethylene oxide; ethoxylated sorbitan fatty acid esters having from 2 to 30 mol of ethylene oxide; saccharose fatty acid esters, polyethylene glycol fatty acid esters, ($C_6$-$C_{24}$)alkylpolyglucocides, N—($C_6$-$C_{24}$)alkylglucamine derivatives, amine oxides, such as ($C_{10}$-$C_{14}$) alkylamine oxides or N—($C_{10}$-$C_{14}$)acylaminopropylmorpholine oxides; and mixtures thereof.=

The amphoteric or zwitterionic surfactant(s) which can be used in the present invention can in particular be optionally quaternized, secondary or tertiary aliphatic amine derivatives in which the aliphatic group is a linear or branched chain comprising from 8 to 22 carbon atoms, the said amine derivatives comprising at least one anionic group, such as, for example, a carboxylic, sulphonate, sulphate, phosphate or phosphonate group. In particular, mention may be made of ($C_8$-$C_{20}$)alkylbetaines, sulphobetaines, ($C_8$-$C_{20}$ alkyl) amido($C_{3-8}$ alkyl)betaines or ($C_8$-$C_{20}$alkyl)amido($C_6$-$C_8$ alkyl)sulphobetaines. Among the optionally quaternized, secondary or tertiary aliphatic amine derivatives that can be used, as defined above, mention may also be made of the compounds having the respective structures (A1) and (A2) below:

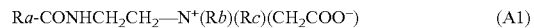

(A1)

in which:

Ra represents a $C_{10}$-$C_{30}$ alkyl or alkenyl group derived from an acid

Ra-COOH, preferably present in hydrolysed coconut oil, a heptyl, nonyl or undecyl group, Rb represents a β-hydroxyethyl group, and Rc represents a carboxymethyl group;

and

(A2)

in which:

B represents —$CH_2CH_2OX'$,

B' represents —$(CH_2)_zY'$, with z=1 or 2,

X' represents the group —$CH_2$—COOH, $CH_2$—COOZ', —$CH_2CH_2$—COOH, —$CH_2CH_2$—COOZ', or a hydrogen atom, Y' represents —COOH, —COOZ', the group —$CH_2$—CHOH—$SO_3H$ or —$CH_2$—CHOH—$SO_3Z'$, Z' represents an ion derived from an alkali metal or alkaline earth metal, such as sodium, an ammonium ion or an ion derived from an organic amine.

Ra' represents a $C_{10}$-$C_{30}$ alkyl or alkenyl group of an acid Ra'-COOH preferably present in hydrolysed linseed oil or coconut oil, an alkyl group, especially a $C_{17}$ alkyl group, and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

The composition according to the invention may also comprise one or more cationic surfactants that are well known per se, such as optionally polyoxyalkylenated, primary, secondary or tertiary fatty amine salts; quaternary ammonium salts such as tetraalkylammonium, alkyl amidoalkyltrialkylammonium, trialkylbenzylammonium, trialkylhydroxyalkylammonium or alkylpyridinium chlorides or bromides; imidazoline derivatives; or amine oxides of cationic nature.

The anionic, nonionic, amphoteric and cationic surfactants described above can be used alone or as mixtures and their amount is between 0.01% and 30% by weight, preferably between 0.05% and 20% by weight and better still between 0.1% and 10% by weight, with respect to the total weight of the composition.

The additional gelling and/or thickening agents other than the (meth)acrylic thickening polymers which are suitable for the compositions of the invention are well known in the art and can be chosen from poly(oxyalkylene)glycols, poly(oxyalkylene)glycol esters, alginates, biosaccharides, celluloses, starch derivatives, natural gums, such as xanthan, guar or locust bean gums, scleroglucans, chitin and chitosan derivatives, carrageenans, clays and mixtures thereof.

The preferred additional gelling agents are chosen from celluloses and guar gums.

The additional gelling agents in general represent from 0.05 to 15%, preferably from 0.5 to 10% by weight of the composition.

The silicones that may be used as additives in the cosmetic compositions of the present invention are volatile or non-volatile, cyclic, linear or branched silicones, optionally modified with organic groups, having a viscosity from $5 \times 10^{-6}$ to $2.5$ m²/s at 25° C. and preferably $1 \times 10^{-5}$ to $1$ m²/s.

The silicones that can be used in accordance with the invention may be soluble or insoluble in the composition and in particular may be polyorganosiloxanes that are insoluble in the composition of the invention. They may be in the form of oils, waxes, resins or gums.

Organopolysiloxanes are defined in greater detail in Walter Noll's "Chemistry and Technology of Silicones" (1968), Academic Press. They may be volatile or non-volatile.

When they are volatile, the silicones are chosen more particularly from those having a boiling point of between 60° C. and 260° C. and more particularly still from:

(i) cyclic silicones containing from 3 to 7 and preferably 4 or 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

with D":

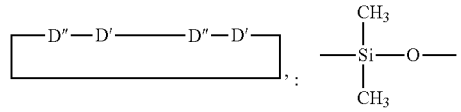

with D':

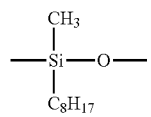

Mention may also be made of mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones containing 2 to 9 silicon atoms and having a viscosity of less than or equal to $5 \times 10^{-6}$ m²/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers "Volatile Silicone Fluids for Cosmetics".

Non-volatile silicones, and more particularly polyalkylsiloxanes, polyarylsiloxanes, polyalkylarylsiloxanes, silicone gums and resins, polyorganosiloxanes modified with organofunctional groups, and mixtures thereof, are preferably used.

These silicones are more particularly chosen from polyalkylsiloxanes, among which mention may be made mainly of polydimethylsiloxanes containing trimethylsilyl end groups. The viscosity of the silicones is measured at 25° C. according to ASTM standard 445 Appendix C.

Among these polyalkylsiloxanes, mention may be made, in a non-limiting manner, of the following commercial products:

the Silbione® oils of the 47 and 70 047 series or the Mirasil® oils sold by Rhodia, such as, for example, the oil 70 047 V 500 000;

the oils of the Mirasil® series sold by the company Rhodia;

the oils of the 200 series from the company Dow Corning, such as DC200 with a viscosity of 60000 mm²/s;

the Viscasil® oils of General Electric and some oils of the SF series (SF 96, SF 18) of General Electric.

Mention may also be made of polymethylsiloxanes containing dimethylsilanol end groups, known by the name dimethiconol (CTFA), such as the oils of the 48 series from the company Rhodia.

In this category of polyalkylsiloxanes, mention may also be made of the products sold under the names Abil Wax® 9800 and 9801 by the company Goldschmidt, which are poly($C_1$-$C_{20}$)alkylsiloxanes.

The polyalkylarylsiloxanes are chosen particularly from linear and/or branched polydimethyl/methylphenylsiloxanes and polydimethyl/diphenylsiloxanes with a viscosity ranging from $1 \times 10^{-5}$ to $5 \times 10^{-2}$ m²/s at 25° C.

Among these polyalkylarylsiloxanes, examples that may be mentioned include the products sold under the following names:

the Silbione® oils of the 70 641 series from Rhodia;
the oils of the Rhodorsil® 70 633 and 763 series from Rhodia;
the Dow Corning 556 Cosmetic Grade Fluid oil from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

The silicone gums that can be used in accordance with the invention are, in particular, polyorganosiloxanes having high number-average molecular weights of between 200000 and 1000000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Mention may be made more particularly of the following products:
- polydimethylsiloxane gums,
- polydimethylsiloxane/methylvinylsiloxane gums,
- polydimethylsiloxane/diphenylsiloxane gums,
- polydimethylsiloxane/phenylmethylsiloxane gums,
- polydimethylsiloxane/diphenylsiloxane/methylvinylsiloxane gums.

Products that can be used more particularly in accordance with the invention are mixtures such as:
- mixtures formed from a polydimethylsiloxane hydroxylated at the end of the chain, or dimethiconol (CTFA), and from a cyclic polydimethylsiloxane, also called cyclomethicone (CTFA), such as the product Q2 1401 sold by the company Dow Corning;
- mixtures formed from a polydimethylsiloxane gum and from a cyclic silicone, such as the product SF 1214 Silicone Fluid from the company General Electric; this product is an SF 30 gum corresponding to a dimethicone, having a number-average molecular weight of 500000, dissolved in the oil SF 1202 Silicone Fluid corresponding to decamethylcyclopentasiloxane;
- mixtures of two PDMSs with different viscosities, and more particularly of a PDMS gum and of a PDMS oil, such as the product SF 1236 from the company General Electric. The product SF 1236 is the mixture of a gum SE 30 defined above with a viscosity of 20 m$^2$/s and of an oil SF 96 with a viscosity of 5×10$^{-6}$ m$^2$/s. This product preferably comprises 15% of gum SE 30 and 85% of an oil SF 96.

The organopolysiloxane resins that can be used in accordance with the invention are crosslinked siloxane systems containing the following units:

$R_2SiO_{2/2}$, $R_3SiO_{1/2}$, $RSiO_{3/2}$ and $SiO_{4/2}$ in which R represents a hydrocarbon-based group containing 1 to 16 carbon atoms or a phenyl group. Among these products, the ones that are particularly preferred are those in which R denotes a lower $C_1$-$C_4$ alkyl group, more particularly methyl, or a phenyl group.

Among these resins, mention may be made of the product sold under the name Dow Corning 593 or those sold under the names Silicone Fluid SS 4230 and SS 4267 by the company General Electric, which are silicones of dimethyl/trimethylsiloxane structure.

Mention may also be made of the resins of the trimethylsiloxysilicate type, sold in particular under the names X22-4914, X21-5034 and X21-5037 by Shin-Etsu.

The organomodified silicones that can be used in accordance with the invention are silicones as defined above and comprising in their structure one or more organofunctional groups attached via a hydrocarbon-based group.

Among the organomodified silicones, mention may be made of polyorganosiloxanes comprising:
- polyethyleneoxy and/or polypropyleneoxy groups optionally containing $C_6$-$C_{24}$ alkyl groups, such as the products known as dimethicone copolyol sold by the company Dow Corning under the name DC 1248 or the oils Silwet® L 722, L 7500, L 77, L 711 from the company Union Carbide and the ($C_{12}$)alkyl methicone copolyol sold by the company Dow Corning under the name Q2 5200;
- substituted or unsubstituted amine groups, such as the products sold under the name GP 4 Silicone Fluid and GP 7100 by the company Genesee or the products sold under the names Q2 8220 and Dow Corning 929 or 939 or Dow Corning 2-8299 by the company Dow Corning or the product sold under the name Belsil ADM LOG 1 by the company Wacker. The substituted amine groups are, in particular, $C_1$-$C_4$ aminoalkyl groups;
- thiol groups such as the products sold under the names GP 72A and GP 71 from Genesee;
- alkoxylated groups such as the product sold under the name Silicone Copolymer F-755 by SWS Silicones and Abil Wax® 2428, 2434 and 2440 by the company Goldschmidt;
- hydroxylated groups such as the polyorganosiloxanes containing a hydroxyalkyl functional group, described in French Patent Application FR-A-8 516 334;
- alkoxyalkyl groups such as, for example, the polyorganosiloxanes described in U.S. Pat. No. 4,957,732;
- anionic groups of the carboxylic type, such as, for example, in the products described in Patent EP 186 507 from the company Chisso Corporation, or of alkylcarboxylic type, such as those present in the product X-22-3701E from the company Shin-Etsu; 2-hydroxyalkylsulphonate; 2-hydroxyalkyl thiosulphate such as the products sold by the company Goldschmidt under the names Abil® 5201 and Abil® 5255;
- hydroxyacrylamino groups, for instance the polyorganosiloxanes described in Patent Application EP 342 834. Mention may be made, for example, of the product Q2-8413 from the company Dow Corning.

The silicones as described above may be used, alone or as a mixture, in an amount of between 0.01% and 20% by weight and preferably between 0.1% and 5% by weight.

The compositions of the invention can also comprise non-silicone fatty substances, such as oils of mineral, vegetable, animal and synthetic origin, waxes, fatty esters, ethoxylated or nonethoxylated fatty alcohols, and non-salified fatty acids.

Mention may be made, as oils which can be used in the composition of the invention, for example, of:
- hydrocarbon-based oils of animal origin, such as perhydrosqualene;
- hydrocarbon-based oils of plant origin, such as liquid fatty acid triglycerides containing from 4 to 10 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil;
- linear or branched hydrocarbons of mineral or synthetic origin, such as volatile or non-volatile liquid paraffins, and derivatives thereof, petroleum jelly, polydecenes, hydrogenated polyisobutene such as Parleam®; isoparaffins, for instance isohexadecane and isodecane;
- partially hydrocarbon-based and/or silicone-based fluoro oils, for instance those described in the document JP-A-2-295 912; fluoro oils that may also be mentioned include perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-(trifluoromethyl)perfluoromorpholine sold under the name PF 5052® by the company 3M.

The wax(es) are selected in particular from carnauba wax, candelilla wax, esparto grass wax, paraffin wax, ozokerite, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cera bellina); other waxes or waxy raw materials that may be used according to the invention are especially marine waxes such as the product sold by the company Sophim under the reference M82, and polyethylene waxes or polyolefin waxes in general.

The saturated or unsaturated fatty acids are more particularly chosen from myristic acid, palmitic acid, stearic acid, behenic acid, oleic acid, linoleic acid, linolenic acid and isostearic acid.

The fatty esters are especially carboxylic acid esters, in particular mono-, di-, tri- or tetracarboxylic esters.

The carboxylic acid esters are especially esters of saturated or unsaturated, linear or branched $C_1$-$C_{26}$ aliphatic acids and of saturated or unsaturated, linear or branched $C_1$-$C_{26}$ aliphatic alcohols, the total carbon number of the esters being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_2$-$C_{26}$ dihydroxy, trihydroxy, tetrahydroxy or pentahydroxy alcohols may also be used.

Mention may especially be made of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate and neopentyl glycol diheptanoate, the esters mentioned above being different from the esters of formula (I).

Among the esters mentioned above, it is preferred to use ethyl and isopropyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

As fatty alcohols, mention may be made of linear or branched, saturated or unsaturated fatty alcohols containing from 8 to 26 carbon atoms, for instance cetyl alcohol, stearyl alcohol and the mixture thereof (cetylstearyl alcohol), octyldodecanol, 2-butyloctanol, 2-hexyldecanol, 2-undecylpentadecanol, oleyl alcohol or linoleyl alcohol.

The fatty substances in general represent from 0.1 to 50%; preferably from 1 to 30%, and more preferably still from 2 to 20% by weight of the total composition.

A person skilled in the art should know how to add the additives without disturbing the properties of the compositions of the invention.

As indicated above, the compositions are preferably provided in the form of gels. Preferably, the compositions have a viscosity of greater than or equal to 4 Pa·s, better still ranging from 4 Pa·s to 500 Pa·s, at a temperature of 25° C. and at a shear rate of 1 $s^{-1}$ (for example measurable with a Haake RS600 rheometer).

The composition according to the invention may especially be used as a leave-in application on the hair.

Another subject-matter of the invention is a method for shaping the hair, comprising the application of a cosmetic composition according to the invention. In particular, the invention relates to a styling method that comprises the application of a composition according to the invention to the hair, optional rinsing of the hair, then shaping and drying of the hair.

The examples that follow illustrate the invention without limiting the scope thereof.

EXAMPLES

The following compositions were produced:
The concentrations are expressed as grams of active materials per 100 grams of composition.

| INCI US | NAME SUPPLIER | A | B | C | D | E | F | G |
|---|---|---|---|---|---|---|---|---|
| Carbomer | Carbopol Ultrez 10 Lubrizol | | | 0.8 | | 0.5 | | |
| Acrylates/$C_{10-30}$ alkyl acrylate crosspolymer | Carbopol Ultrez 21 polymer Lubrizol | 0.7 | 1 | | 0.8 | | 0.7 | |
| Hydroxypropyl guar | Jaguar HP105 Rhodia | | | | | 0.2 | 0.2 | |
| Hydroxypropylcellulose | Klucel MF Pharm Aqualon | | | | | | | 1 |
| Acrylates/t-butylacrylamide copolymer | Ultrahold Strong BASF | | | | | | | 4 |

-continued

| INCI US | NAME SUPPLIER | A | B | C | D | E | F | G |
|---|---|---|---|---|---|---|---|---|
| VP/VA copolymer | Luviskol VA 64 W | | | 0.7 | | | | |
| VP/dimethylaminoethyl methacrylate copolymer | Copolymer 845 O ISP | 2.5 | 2 | | | | | |
| Vinylcaprolactam/VP/ dimethylaminoethyl methacrylate copolymer | Advantage HC 37 ISP | | | | 2 | | | |
| Polyquaternium-46 | Luviquat Hold | | | | | 0.8 | | |
| AMP-acrylates/allyl methacrylate copolymer | Fixate G100 L Lubrizol | | | | | | 1.3 | |
| PEG-14 dimethicone | Abil B 8842 Evonik Goldschmidt | | | 0.1 | | | | |
| Glycerol | Glycerine 4810 Oleon | | | | | 3 | | |
| Propylene glycol | Propylene glycol US/EP Dow Chemical | | | | 2 | | | |
| Piroctone olamine | Octopirox Clariant | | 0.3 | | | | | |
| Dipotassium glycyrrhizate | Dipotassium glycyrrhizate Maruzen | | | | | | 0.2 | 0.2 |
| Niacinamide | Niacinamide USP Vertellus | | | 0.05 | | | | |
| Panthenol | D-Panthenol USP BASF | | | 0.05 | | | | |
| Fragrance | Fragrance | 0.3 | 0.4 | 0.3 | 0.3 | 0.4 | 0.4 | 0.4 |
| Aminomethyl propanol | AMP Ultra PC 3000 Angus | 0.5 | 0.6 | 0.4 | 0.5 | 0.4 | 0.6 | 0.4 |
| Alcohol | Ethanol SDA 40B 200 proof Sasol | 75 | 80 | 85 | 70 | 82 | 88 | 80 |
| Water | Water | q.s. 100 | q.s. for 100 | q.s. for 100 | q.s. for 100 | q.s. for 100 | q.s. for 100 | q.s. for 100 |

These compositions are provided in the form of gels which, in application, are easily distributed over the hair without a tacky effect. Drying is rapid.

The fixing of the hair is natural.

The invention claimed is:

1. A cosmetic composition comprising:
   (i) one or more cationic fixing polymers;
   (ii) one or more (meth)acrylic thickening polymers other than the fixing polymer or polymers (i) chosen from acrylic associative thickeners, crosslinked acrylic acid homopolymers, or crosslinked copolymers of (meth) acrylic acid and of ($C_1$-$C_6$)alkyl acrylate;
   (iii) from 5 to 27% by weight of water, with respect to the total weight of the cosmetic composition; and
   (iv) from 70 to 90% by weight of one or more $C_1$ to $C_6$ alcohols, with respect to the total weight of the cosmetic composition.

2. The cosmetic composition according to claim 1, wherein the (meth)acrylic thickening polymer or polymers are anionic.

3. The cosmetic composition according to claim 1, comprising from 0.05 to 20% by weight of one or more (meth) acrylic thickening polymers, with respect to the total weight of the composition.

4. The composition according to claim 1, comprising from 0.1 to 10% by weight of one or more (meth)acrylic thickening polymers, with respect to the total weight of the composition.

5. The composition according to claim 1, comprising from 0.3 to 5% by weight of one or more (meth)acrylic thickening polymers, with respect to the total weight of the composition.

6. The cosmetic composition according to claim 1, comprising water in an amount ranging from 5 to 15% by weight, with respect to the total weight of the composition.

7. The cosmetic composition according to claim 1, comprising one or more $C_2$ to $C_6$ alcohols in an amount ranging from 75 to 85% with respect to the total weight of the composition.

8. The cosmetic composition according to claim 1, wherein the $C_2$ to $C_6$ alcohol is a monoalcohol.

9. The cosmetic composition according to claim 1, wherein the $C_2$ to $C_6$ alcohol is chosen from ethanol and isopropanol.

10. The cosmetic composition according to claim 1, wherein the $C_2$ to $C_6$ alcohol is ethanol.

11. The cosmetic composition according to claim 1, wherein the cosmetic composition is in the form of a gel.

12. The cosmetic composition according to claim 1, having a viscosity of greater than or equal to 4 Pa·s, at a temperature of 25° C. and at a shear rate of 1 $s^{-1}$.

13. The cosmetic composition according to claim 1, having a viscosity ranging from 4 Pa·s to 500 Pa·s, at a temperature of 25° C. and at a shear rate of 1 $s^{-1}$.

14. A method of styling hair comprising:

applying to the hair cosmetic composition comprising:
- (i) one or more cationic fixing polymers;
- (ii) one or more (meth)acrylic thickening polymers other than the fixing polymer or polymers (i) chosen from acrylic associative thickeners, crosslinked acrylic acid homopolymers, or crosslinked copolymers of (meth)acrylic acid and of $(C_1\text{-}C_6)$alkyl acrylate;
- (iii) from 5 to 27% by weight of water, with respect to the total weight of the cosmetic composition; and
- (iv) from 70 to 90% by weight of one or more $C_1$ to $C_6$ alcohols, with respect to the total weight of the cosmetic composition;

optionally rinsing the hair; and optionally shaping and drying the hair.

\* \* \* \* \*